United States Patent
Stappers et al.

(10) Patent No.: US 10,774,088 B2
(45) Date of Patent: Sep. 15, 2020

(54) SIMPLIFIED PROCEDURE FOR THE PREPARATION OF DARUNAVIR

(71) Applicant: Janssen Sciences Ireland Unlimited Company, County Cork (IE)

(72) Inventors: Alfred Elisabeth Stappers, Oud-Turnhout (BE); Yolande Lydia Lang, Vosselaar (BE); Shane Barry Robinson, Midleton (IE)

(73) Assignee: Janssen Sciences Ireland Unlimited Company, Co Cork (IE)

( * ) Notice: Subject to any disclaimer, the term of this patent is extended or adjusted under 35 U.S.C. 154(b) by 0 days.

(21) Appl. No.: 16/461,754

(22) PCT Filed: Nov. 16, 2017

(86) PCT No.: PCT/EP2017/079375
§ 371 (c)(1),
(2) Date: May 16, 2019

(87) PCT Pub. No.: WO2018/091559
PCT Pub. Date: May 24, 2018

(65) Prior Publication Data
US 2019/0359625 A1    Nov. 28, 2019

(30) Foreign Application Priority Data

Nov. 17, 2016 (EP) .................................. 16199275

(51) Int. Cl.
*C07D 493/04* (2006.01)

(52) U.S. Cl.
CPC .................................. *C07D 493/04* (2013.01)

(58) Field of Classification Search
CPC .................................................... C07D 493/04
USPC ........................................................ 549/464
See application file for complete search history.

(56) References Cited

FOREIGN PATENT DOCUMENTS

| WO | WO 2005/063770 A1 | 7/2005 |
| WO | WO 2009/055006 A1 | 4/2009 |
| WO | WO 2014/016660 A1 | 1/2014 |

OTHER PUBLICATIONS

International Search Report and Written Opinion dated Dec. 20, 2017 for International Application PCT/EP2017/079375.
Surleraux, Dominique L. N. G. et al., Discovery and Selection of TMC114, a Next Generation HIV-1 Protease Inhibitor, J. Med. Chem. 2005, 48, pp. 1813-1822.

*Primary Examiner* — Taylor V Oh

(57) ABSTRACT

The present invention relates to an improved process for preparing [(1S,2R)-3-[[(4-aminophenyl)-sulfonyl](2-methyl-propyl)amino]-2-hydroxy-1-(phenylmethyl)-propyl]-carbamic acid (3R,3aS,6aR)-hexahydrofuro[2,3-b]furan-3-yl ester—which compound is also known under its INN as darunavir—by reacting carbonic acid 2,5-dioxo-1-pyrrolidinyl[(3R,3aS,6aR)-hexahydrofuro[2,3-b]furan-3-yl] ester with 4-amino-N-[(2R,3S)-3-amino-2-hydroxy-4-phenylbutyl]-N-(2-methylpropyl)-benzenesulfonamide in ethanol as solvent. Furthermore said process allows for darunavir to be isolated immediately in its ethanolate form, i.e. darunavir monoethanolate, which is the marketed form of darunavir under the tradename Prezista™.

17 Claims, No Drawings

SIMPLIFIED PROCEDURE FOR THE PREPARATION OF DARUNAVIR

CROSS-REFERENCE TO RELATED APPLICATIONS

This application is a 371 national phase entry of International Application No. PCT/EP2017/079375, filed on Nov. 16, 2017, which claims priority to European Patent Application No. 16199275.5, filed Nov. 17, 2016, both of which are incorporated herein in their entirety.

FIELD OF THE INVENTION

The present invention relates to an improved process for preparing [(1S,2R)-3-[[(4-aminophenyl)-sulfonyl](2-methylpropyl)amino]-2-hydroxy-1-(phenylmethyl)-propyl]-carbamic acid (3R,3aS,6aR)-hexahydrofuro[2,3-b]furan-3-yl ester—which compound is also known under its INN as darunavir—by reacting carbonic acid 2,5-dioxo-1-pyrrolidinyl [(3R,3aS,6aR)-hexahydrofuro[2,3-b]furan-3-yl]ester with 4-amino-N-[(2R,3S)-3-amino-2-hydroxy-4-phenylbutyl]-N-(2-methylpropyl)-benzenesulfonamide in ethanol as solvent. Furthermore said process allows for darunavir to be isolated immediately in its ethanolate form, i.e. darunavir monoethanolate, which is the marketed form of darunavir under the tradename Prezista™.

BACKGROUND OF THE INVENTION

Darunavir is a nonpeptidic protease inhibitor approved for use in the treatment of human immunodeficiency virus type 1 (HIV-1) infection and has the following chemical structure:

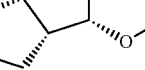

WO-2005/063770 discloses in Examples 7 a process for preparing darunavir by reacting carbonic acid 2,5-dioxo-1-pyrrolidinyl [(3R,3aS,6aR)-hexahydrofuro[2,3-b]furan-3-yl]ester [referenced throughout this text as compound (A)], that was first prepared in situ, with 4-amino-N-[(2R,3S)-3-amino-2-hydroxy-4-phenylbutyl]-N-(2-methylpropyl)-benzenesulfonamide [referenced throughout this text as compound (B)] in ethyl acetate as solvent to which triethylamine was added as a base. The reaction was quenched by addition of methylamine in an aqueous solution in ethanol. The crude darunavir isolated from the reaction mixture was converted into its ethanolate form by crystallization from absolute ethanol with a yield of 71%.

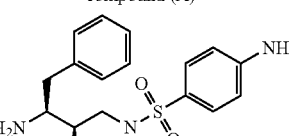

compound (A)

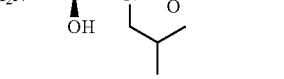

WO-2005/063770 discloses in Examples 9 a process for preparing darunavir by reacting compound (A), that was first prepared in situ, with compound (B) in acetonitril as solvent to which triethylamine was added as a base. The reaction was quenched by addition of methylamine in an aqueous solution in ethanol. The crude darunavir isolated from the reaction mixture was converted into its ethanolate form by crystallization from absolute ethanol with a yield of 81%.

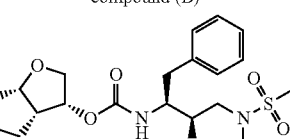

compound (A)

Journal of Medicinal Chemistry, vol. 48, p. 1813-1822 (2005) discloses the synthesis of darunavir as compound (1a) by reacting compound (A) with compound (B) in dichloromethane as solvent in the presence of triethylamine as a base with a yield of 90%.

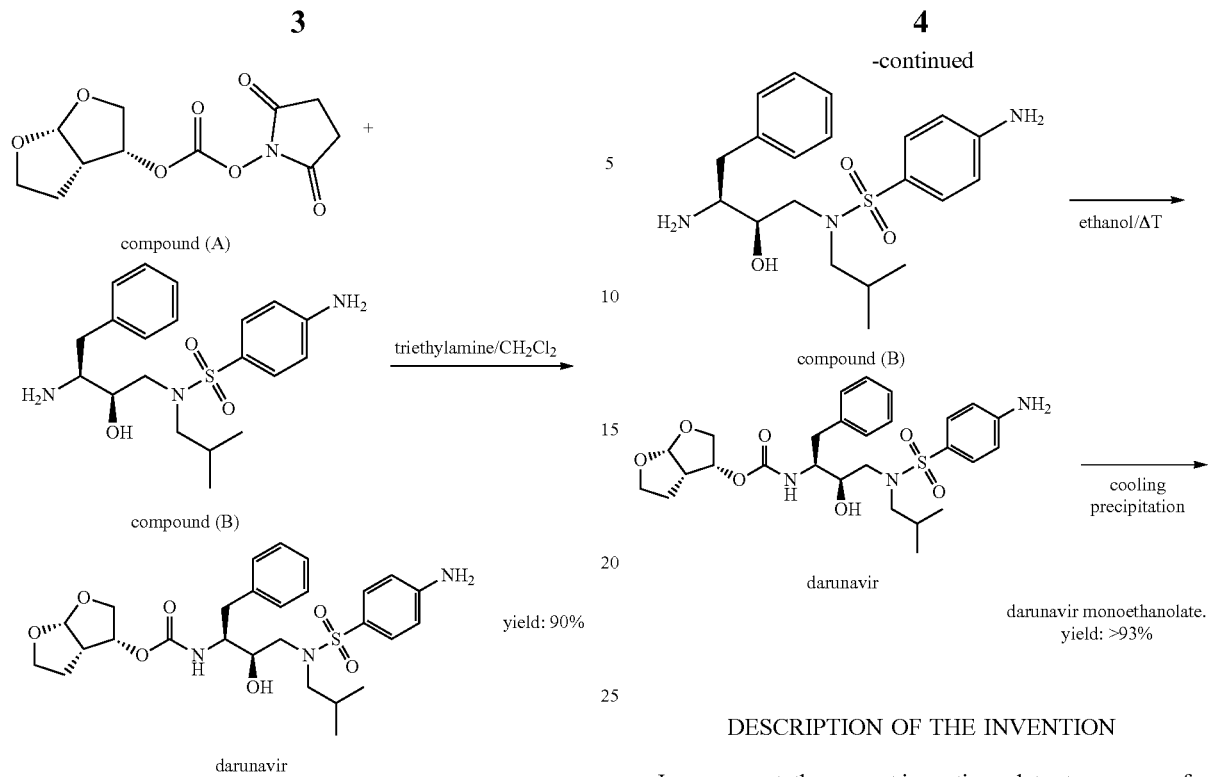

WO-2009/055006 discloses a process for preparing a deuterated form of darunavir by reacting carbonic acid 2,5-dioxo-1-pyrrolidinyl [(3R,3aS,6aR)-hexahydrofuro[2,3-b]furan-3-yl]ester with a deuterated form of 4-amino-N-[(2R,3S)-3-amino-2-hydroxy-4-phenylbutyl]-N-(2-methylpropyl)-benzenesulfonamide in dichloromethane as solvent in the presence of triethylamine as a base.

WO-2014/016660 discloses in Example 3 a process for preparing darunavir in its propionate solvate form by reacting carbonic acid 2,5-dioxo-1-pyrrolidinyl [(3R,3 aS,6aR)-hexahydrofuro[2,3-b]furan-3-yl]ester with 4-amino-N-[(2R,3S)-3-amino-2-hydroxy-4-phenylbutyl]-N-(2-methylpropyl)-benzenesulfonamide in a two phase mixture of ethyl acetate and water, followed by salt conversion with propionic acid with an overall yield of 90%.

It now has been found that darunavir can be obtained in a simplified procedure by reacting carbonic acid 2,5-dioxo-1-pyrrolidinyl [(3R,3aS,6aR)-hexahydrofuro[2,3-b]furan-3-yl]ester, i.e. compound (A), with 4-amino-N-[(2R,3S)-3-amino-2-hydroxy-4-phenylbutyl]-N-(2-methylpropyl)-benzenesulfonamide, i.e. compound (B), in the absence of an organic base and ethanol as solvent while heating. Upon completion of the reaction, the reaction mixture is heated till homogeneous and then allowed to cool to ambient temperature whereby darunavir crystallizes in its monoethanolate form.

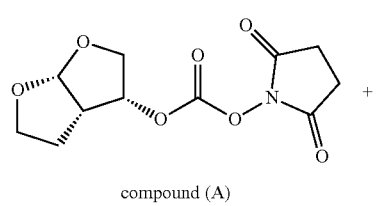

compound (A)

DESCRIPTION OF THE INVENTION

In one aspect, the present invention relates to a process for preparing darunavir, which process comprises the steps of
a) reacting carbonic acid 2,5-dioxo-1-pyrrolidinyl [(3R,3aS, 6aR)-hexahydrofuro[2,3-b]furan-3-yl]ester with 4-amino-N-[(2R,3S)-3-amino-2-hydroxy-4-phenylbutyl]-N-(2-methylpropyl)-benzenesulfonamide in ethanol as solvent while heating the reaction mixture at a temperature between 30° C. and reflux temperature.

In a further aspect, the present invention relates to a process for preparing darunavir, which process comprises the steps of
a) reacting carbonic acid 2,5-dioxo-1-pyrrolidinyl [(3R,3aS, 6aR)-hexahydrofuro[2,3-b]furan-3-yl]ester with 4-amino-N-[(2R,3S)-3-amino-2-hydroxy-4-phenylbutyl]-N-(2-methylpropyl)-benzenesulfonamide in the absence of an organic base and ethanol as solvent while heating the reaction mixture at a temperature between 30° C. and reflux temperature.

In a further aspect, the present invention relates to a process for preparing the monoethanolate form of darunavir, which process comprises the steps of
a) reacting carbonic acid 2,5-dioxo-1-pyrrolidinyl [(3R,3aS, 6aR)-hexahydrofuro[2,3-b]furan-3-yl]ester with 4-amino-N-[(2R,3S)-3-amino-2-hydroxy-4-phenylbutyl]-N-(2-methylpropyl)-benzenesulfonamide in the absence of an organic base and ethanol as solvent while heating the reaction mixture at a temperature between 30° C. and reflux temperature;
b) upon completion of the reaction, heating the reaction mixture heating till homogeneous;
c) cooling the reaction mixture;
d) isolating the precipitated product;
e) crystallizing the thus obtained precipitated product from ethanol; and
f) isolating the crystallized darunavir monoethanolate.

In step a) the reaction mixture is heated to a temperature between the ambient temperature and the reflux temperature such as between 20° C. and 78° C., or between 30° C. and reflux temperature, or between 30° C. and 78° C., or between 30° C. and 70° C., or between 40° and 60° C. It is well known to the skilled person that the reaction rate increases when the reaction is performed at a higher temperature. Progress and completion of the reaction can be monitored by the skilled person by taking samples at regular moments and analyzing these samples e.g. by thin layer chromatograpy or HPLC.

The process for preparing darunavir according to the present invention can be performed without the presence of an organic base. An organic base is used to capture any acid product formed during the reaction. Well known examples are e.g. trimethylamine, triethylamine, pyridine, and the like.

This simplified procedure for the preparation of darunavir has the following advantages over the art known procedures:
- no use of hazardous chlorinated solvents such as dichloromethane,
- no use of poisonous solvents such as acetonitrile,
- no use of an organic base such as triethylamine or pyridine, the removal of which can be very laborious in large scale production;
- high yield;
- upon cooling of the reaction mixture darunavir precipitates in the form of its monoethanolate form which can be easily isolated and recrystallized from ethanol to obtain darunavir monoethanolate that is of sufficient purity to be used—i.e. without the need of additional purification steps—as the API (active pharmaceutical ingredient) in commercial products such as Prezista™.

The use of ethanol as solvent for the reaction between compound (A) and compound (B) is not obvious for the skilled person since the skilled person expects that compound (A) would react with the protic solvent ethanol that is present in great abundance through a competitive side-reaction to form the undesired side-product (C). Only minute amounts of side-product (C)—less than 0.5% relative to compound (A)—have been observed and the almost absence of a competitive side-reaction of compound (A) with ethanol is an unexpected surprise to the skilled person.

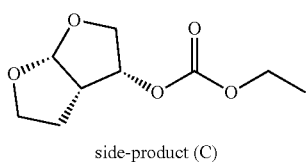

side-product (C)

When compound (A) and compound (B) are added to the ethanol solvent in the reactor at ambient temperature, the reaction mixture is heterogeneous. Stirring and heating of the reaction mixture is continued until the reaction of compound (A) and compound (B) is complete. Upon warming to the reflux temperature of the solvent (i.e. 78° C. for ethanol) the reaction mixture becomes homogeneous.

The molar ratio compound (A) and compound (B) may range from 0.95 to 1.05.

When the reaction of compound (A) and compound (B) is complete the reaction mixture is slowly cooled to a temperature between 15° C. and −10° C. during which a solid product precipitates from the reaction mixture. The precipitated product is then isolated from the reaction mixture and can be further purified by recrystallization from ethanol to obtain pure darunavir monoethanolate.

Rerystallization of the obtained precipitated product is performed by suspending the precipitated product in ethanol, heating the resulting mixture until a homogeneous solution is obtained, followed by cooling to ambient temperature or a temperature between −5° C. and 25° C. The cooling of the crystallization mixture may be done by natural cooling or according to a specific temperature cooling profile. For instance the temperature cooling profile may be a linear profile, e.g. 0.1° C./minute, 0.3° C./minute, 0.5° C./minute, 0.75° C./minute, 1° C./minute, 2° C./minute or any other value. Alternatively, a cubic cooling profile may be used. During cooling seed crystals of darunavir monoethanolate may be added.

The cooling procedure of the crystallization mixture can also include an Ostwald ripening procedure, also called temperature cycling procedure, whereby the crystallization mixture after seeding is cooled to a certain temperature, then reheated and again cooled to a certain temperature, before the crystallization mixture is allowed to cool to ambient temperature. Such an Ostwald ripening procedure can improve the morphology of the darunavir monoethanolate crystals. In practice, the following Ostwald ripening procedure is used:
- keep crystallization mixture at a temperature between 61° C. and 63° C. for a period of 20 to 40 minutes,
- cool crystallization mixture to a temperature between 57° C. and 59° C. over a period of 5 to 20 minutes,
- keep crystallization mixture at a temperature between 57° C. and 59° C. over a period of 20 to 40 minutes,
- heat crystallization mixture to a temperature between 66° C. and 68° C. over a period of 5 to 20 minutes,
- keep crystallization mixture at a temperature between 66° C. and 68° C. over a period of 20 to 40 minutes.

The Ostwald ripening procedure can be repeated until the desired morphology of the darunavir monoethanolate crystals is obtained.

The isolation of the darunavir monoethanolate crystals can be carried out by any conventional means, such as by filtration or centrifugation.

The process for preparing darunavir monoethanolate according to the present invention can be used in batch chemical processes and also in semi-continuous production or continuous chemical production (also known as continuous manufacturing).

The process for preparing darunavir monoethanolate according to the present invention may also be performed in another alcohol than ethanol, such as e.g. isopropanol, propanol, butanol, and the like. Such a process should be followed by an additional step to convert the obtained darunavir alcoholate into darunavir monoethanolate.

EXPERIMENTAL PART

Analytical Analysis

The presence of side-product (C)

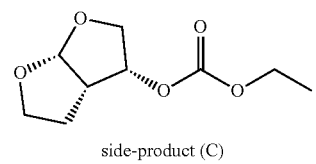

side-product (C)

was determined using gas chromatography using the following conditions:

| | |
|---|---|
| Column | RXi-HT 30 m length × 0.32 mm i.d. 0.1 μm particle size or equivalent |
| Inlet temperature | 200° C. |
| Inlet mode | split mode:split ratio 45:1 liner: Agilent 210-4004-5 |
| Injection volume | 2 μl |
| Autosampler | wash solvent A: acetonitrile wash solvent B: acetonitrile solvent A pre-wash: 6 times solvent B pre-wash: 0 times sample wash: 0 times injection pumps: 6 times solvent A post-wash: 0 times solvent B post-wash: 6 times |
| Carrier gas, flow rate | hydrogen; 1.5 ml/min |
| Over temperature | 40° C. progam run: 30° C./min till 310° C. |
| Detector | FID |
| Detector temperature | 320° C. |
| Dilution solvent | acetonitrile |

Example 1

4-Amino-N-[(2R,3S)-3-amino-2-hydroxy-4-phenylbutyl]-N-(2-methylpropyl)-benzenesulfonamide (39.2 g; 0.1 mol) and ethanol (170 ml) were added to a 1 litre reaction vessel. The reaction mixture was stirred over 15 minutes at 20° C. and carbonic acid 2,5-dioxo-1-pyrrolidinyl [(3R,3aS,6aR)-hexahydrofuro [2,3-b]furan-3-yl]ester (26.6 g; 0.098 mol) was added at 20° C. The reaction mixture was heated up to 50° C. over a period of 30 minutes to 1 hour and stirred over 2 hours at that temperature. The reaction mixture was heated to 78° C. (reflux) over 30 minutes and stirred for 10 minutes.

The reaction mixture was cooled to −5° C. over a period 4.5 hours (+/−0.3° C./min.) during which spontaneous crystallization occurred. The reaction mixture was filtered and the precipitate was washed twice with ethanol (2×40 ml).

The precipitate was dissolved in ethanol (212 ml) and the mixture was heated to 78° C. (reflux) over 60 minutes. The reaction mixture was cooled to 62° C. over a period of 30 minutes (+/−0.5° C./min.) and seeded with crystalline darunavir monoethanolate (120 mg). The reaction mixture was stirred at 62° C. over 90 minutes, cooled to 50° C. over 2 hours (0.1° C./min.), further cooled to 15° C. over 1 hour 30 minutes (cooling rate of about 0.3° C./minute) and stirred at 15° C. over a period of 1 hour to 12 hours. The reaction mixture was filtered and the white precipitate was washed twice with EtOH (2×60 ml). The precipitate was dried under vacuum (40° C., 12 hours), yielding 55.2 g (93%) of darunavir monoethanolate.

The presence of side-product (C) was determined using the analytical procedure described above and it was found to be less than 0.5% relative to darunavir monoethanolate.

Example 2

4-Amino-N-[(2R,3S)-3-amino-2-hydroxy-4-phenylbutyl]-N-(2-methylpropyl)-benzenesulfonamide (39.2 g; 0.1 mol) and ethanol (170 ml) were added to a 1 litre reaction vessel. The reaction mixture was stirred over 15 minutes at 20° C. and carbonic acid 2,5-dioxo-1-pyrrolidinyl [(3R,3aS,6aR)-hexahydrofuro [2,3-b]furan-3-yl]ester (26.6 g; 0.098 mol) was added at 20° C. The reaction mixture was heated up to 50° C. over a period of 30 minutes to 1 hour and stirred over 2 hours at that temperature. The reaction mixture was heated to 78° C. (reflux) over 30 minutes and stirred for 10 minutes.

The reaction mixture was cooled to 15° C. over a period 3.5 hours (+/−0.3° C./min.) during which spontaneous crystallization occurred. The reaction mixture was filtered and the precipitate was washed twice with ethanol (2×40 ml).

The precipitate was dissolved in ethanol (212 ml) and the mixture was heated to 78° C. (reflux) over 60 minutes. The reaction mixture was cooled to 62° C. over a period of 30 minutes (+/−0.5° C./min.) and seeded with crystalline darunavir monoethanolate (120 mg). The reaction mixture was stirred at 62° C. over 90 minutes, cooled to 50° C. over 2 hours (0.1° C./min.), further cooled to 15° C. over 1 hour 30 minutes (cooling rate of about 0.3° C./minute) and stirred at 15° C. over a period of 1 hour to 12 hours. The reaction mixture was filtered and the white precipitate was washed twice with EtOH (2×60 ml). The precipitate was dried under vacuum (40° C., 12 hours), yielding 55.2 g (93%) of darunavir monoethanolate.

The presence of side-product (C) was determined using the analytical procedure described above and it was found to be less than 0.5% relative to darunavir monoethanolate.

Example 3

4-Amino-N-[(2R,3S)-3-amino-2-hydroxy-4-phenylbutyl]-N-(2-methylpropyl)-benzenesulfonamide (39.2 g; 0.1 mol) and ethanol (170 ml) were added to a 1 litre reaction vessel. The reaction mixture was stirred over 15 minutes at 20° C. and carbonic acid 2,5-dioxo-1-pyrrolidinyl [(3R,3aS,6aR)-hexahydrofuro [2,3-b]furan-3-yl]ester (26.6 g; 0.098 mol) was added at 20° C. The reaction mixture was heated up to 50° C. over a period of 30 minutes to 1 hour and stirred over 2 hours at that temperature. The reaction mixture was heated to 78° C. (reflux) over 30 minutes and stirred for 10 minutes.

The reaction mixture was cooled to 15° C. over a period 3.5 hours (+/−0.3° C./min.) during which spontaneous crystallization occurred. The reaction mixture was filtered and the precipitate was washed twice with ethanol (2×40 ml).

The precipitate was dissolved in ethanol (212 ml) and the mixture was heated to 78° C. (reflux) over 60 minutes. The reaction mixture was cooled to 62° C. over a period of 30 minutes (+/−0.5° C./min.) and seeded with crystalline darunavir monoethanolate (120 mg). The reaction mixture was stirred at 62° C. for 30 minutes, cooled to 58° C. over a period of 10 minutes and hold for 30 minutes, heated to 67° C. over a period of 10 minutes and hold for 30 minutes and then cooled to 50° C. over 2 hours (0.1° C./min.), further cooled to 15° C. over 1 hour 30 minutes (cooling rate of about 0.3° C./minute) and stirred at 15° C. over a period of 1 hour to 12 hours. The reaction mixture was filtered and the white precipitate was washed twice with EtOH (2×60 ml). The precipitate was dried under vacuum (40° C., 12 hours), yielding 55.2 g (93%) of darunavir monoethanolate.

The presence of side-product (C) was determined using the analytical procedure described above and it was found to be less than 0.5% relative to darunavir monoethanolate.

Example 4

4-Amino-N-[(2R,3S)-3-amino-2-hydroxy-4-phenylbutyl]-N-(2-methylpropyl)-benzenesulfonamide (39.2 g; 0.1 mol) and ethanol (220 ml) were added to a 1 litre reaction vessel. After stirring for 10 minutes at 10° C. carbonic acid 2,5-dioxo-1-pyrrolidinyl [(3R,3aS,6aR)-hexahydrofuro[2,3-b]furan-3-yl]ester (26.6 g; 0.098 mol) was added. The reaction mixture was homogenized with a high shear lab mixer for 4 minutes at 10° C. This slurry was used as a feed for a tube flow reactor. The reaction was completed after 30 seconds at 80° C. The in situ quality is identical to the batch process examples 1 to 3.

The presence of side-product (C) was determined using the analytical procedure described above and it was found to be less than 0.5% relative to darunavir monoethanolate.

The invention claimed is:

1. A process for preparing darunavir, which process comprises the step of
   a) reacting carbonic acid 2,5-dioxo-1-pyrrolidinyl [(3R,3aS,6aR)-hexahydrofuro[2,3-b]furan-3-yl]ester with 4-amino-N-[(2R,3S)-3-amino-2-hydroxy-4-phenylbutyl]-N-(2-methylpropyl)-benzenesulfonamide in ethanol while heating the reaction mixture at a temperature between 30° C. and reflux temperature.

2. The process according to claim 1 wherein step a) is carried out in the absence of an organic base.

3. The process according to claim 2 wherein the molar ratio of carbonic acid 2,5-dioxo-1-pyrrolidinyl [(3R,3aS,6aR)-hexahydrofuro[2,3-b]furan-3-yl]ester and 4-amino-N-[(2R,3S)-3-amino-2-hydroxy-4-phenylbutyl]-N-(2-methylpropyl)-benzenesulfonamide ranges from 0.95 to 1.05.

4. The process according to claim 3 wherein step a) is carried out at a temperature between 30° C. and 70° C.

5. The process according to claim 4 wherein the temperature is between 40° and 60° C.

6. The process according to claim 1 whereby step a) is followed by the following steps:
   b) heating till the reaction mixture is homogeneous;
   c) cooling the reaction mixture;
   d) isolating the precipitated product;
   e) crystallizing the thus obtained precipitated product from ethanol; and
   f) isolating the crystallized darunavir monoethanolate.

7. The process according to claim 6 wherein the reaction mixture in step b) is cooled to a temperature between 15° C. and −10° C.

8. The process according to claim 6 wherein the crystallization of the obtained precipitated product is performed by suspending the precipitated product in ethanol, heating the resulting mixture until a homogeneous solution is obtained, followed by cooling.

9. The process according to claim 8 wherein the crystallization comprises a temperature cycling procedure.

10. The process according to claim 9 wherein the temperature cycling procedure comprises the steps of:
    keeping the crystallization mixture at a temperature between 61° C. and 63° C. for a period of 20 to 40 minutes,
    cooling the crystallization mixture to a temperature between 57° C. and 59° C. over a period of 5 to 20 minutes,
    keeping the crystallization mixture at a temperature between 57° C. and 59° C. for a period of 20 to 40 minutes.
    heating the crystallization mixture to a temperature between 66° C. and 68° C. over a period of 5 to 20 minutes, and
    keeping the crystallization mixture at a temperature between 66° C. and 68° C. for a period of 20 to 40 minutes.

11. The process according to claim 8 wherein cooling is done by natural cooling.

12. The process according to claim 8 wherein cooling is done following a linear cooling profile.

13. The process according to claim 11 wherein the crystallization mixture is cooled to a temperature between −5° C. and 25° C. before the darunavir monoethanolate crystals are isolated.

14. A process for preparing darunavir, which process comprises the steps of
    a) reacting carbonic acid 2,5-dioxo-1-pyrrolidinyl [(3R,3aS,6aR)-hexahydrofuro[2,3-b]furan-3-yl]ester with 4-amino-N-[(2R,3S)-3-amino-2-hydroxy-4-phenylbutyl]-N-(2-methylpropyl)-benzenesulfonamide in ethanol while heating the reaction mixture at a temperature between 30° C. and reflux temperature;
    b) heating till the reaction mixture is homogeneous;
    c) cooling the reaction mixture;
    d) isolating the precipitated product;
    e) crystallizing the thus obtained precipitated product from ethanol; and
    f) isolating the crystallized darunavir monoethanolate.

15. The process according to claim 14 wherein the reaction mixture in step b) is cooled to a temperature between 15° C. and −10° C.

16. The process according to claim 15 wherein the crystallization comprises a temperature cycling procedure.

17. The process according to claim 16 wherein the temperature cycling procedure comprises the steps of:
    keeping the crystallization mixture at a temperature between 61° C. and 63° C. for a period of 20 to 40 minutes,
    cooling the crystallization mixture to a temperature between 57° C. and 59° C. over a period of 5 to 20 minutes,
    keeping the crystallization mixture at a temperature between 57° C. and 59° C. for a period of 20 to 40 minutes.
    heating the crystallization mixture to a temperature between 66° C. and 68° C. over a period of 5 to 20 minutes, and
    keeping the crystallization mixture at a temperature between 66° C. and 68° C. for a period of 20 to 40 minutes.

* * * * *